(12) United States Patent
Benistant et al.

(10) Patent No.: US 6,759,204 B2
(45) Date of Patent: Jul. 6, 2004

(54) METHOD AND KIT FOR EARLY DIAGNOSIS OF CANCER

(75) Inventors: Christine Benistant, Maguelonne (FR); Heliette Chapuis, Bellegarde (FR); Nicolas Mottet-Auselo, Nîmes (FR); Serge Roche, Montpellier (FR); Jean-François Bourgaux, Montpellier (FR); Jean-Pierre Bali, Saint Gely de Fesc (FR)

(73) Assignee: Centre National de la Recherche Scientifique-CNRS (FR)

( * ) Notice: Subject to any disclaimer, the term of this patent is extended or adjusted under 35 U.S.C. 154(b) by 0 days.

(21) Appl. No.: 09/737,351

(22) Filed: Dec. 15, 2000

(65) Prior Publication Data

US 2001/0005582 A1 Jun. 28, 2001

Related U.S. Application Data

(63) Continuation of application No. PCT/FR99/01444, filed on Jun. 16, 1999.

(30) Foreign Application Priority Data

Jun. 17, 1998 (FR) ............................................. 98 07655

(51) Int. Cl.$^7$ ................................................. G01N 33/53
(52) U.S. Cl. ................. 435/7.1; 530/387.7; 530/388.26
(58) Field of Search .......................... 514/44; 536/24.1, 536/24.3; 435/7.2, 7.21, 7.1; 530/388.26, 388.8, 387.7, 350

(56) References Cited

FOREIGN PATENT DOCUMENTS

| WO | 92 02187 A | 1/1995 |
|----|------------|--------|
| WO | 95 24205 A | 9/1995 |

OTHER PUBLICATIONS

Cam WR, et al. Cancer 2001; 92: 61–70.*
Sakai et al (Lab Invest., Feb. 1998, vol. 78(2):219–25, abstract).*
Verbeek et al (J. Pathol., 1996, vol. 180(4):383–8, abstract).*
Iravani et al (Lab Invest., Mar. 1998, vol. 78(3):365–71, abstract).*
Tockman, MS, et al, 1992, Considerations in bringing a cancer biomarker to clinical application, Cancer Research, vol. 52, Suppl., pp. 2711s–2718s.*
Bjorge, JD, et al, 2000, Identification of protein–tyrosine phosphatase 1B as the major tyrosine phophatase activity capable of dephosporylating and activating c–src, Journal of Biological Chemistry, vol. 275, No. 52, pp. 41439–41446.*
Bougeret, C, et al, 1996, Detection of a physical and functional interaction between Csk and Lck which involves the SH2 domain of Csk and is mediated by autophosphorylation of Lck, Journal of Biological Chemistry, vol. 271, No. 13, pp. 7465–7472.*
Benistant, C, et al, 2001, THe COOH–terminal Src kinase Csk is a tumor antigen in human carcinoma, Cancer Research, vol. 61, No. 4, pp. 1415–1420.*
Masaki, T, et al, 1999, Reduced C–terminal Src kinase (Csk) activities in hepatocellular carcinoma, Hepatology, vol. 29, No. 2, pp. 379–384.*
Montenarh, M, et al, 1998, p53 autoantibodies in the sera, cytst and ascitic fluids of patients with ovarian cancer, International Journal of Oncology, vol. 13, No. 3, pp. 605–610.*
Marx, D, et al, 2001, Detection of serum autoantibodies to tumor suppressor gene p53 with a new enzyme–linked immunosorbent assay in patients with ovarian cancer, Cancer Detection and Prevention, vol. 25, No. 2, pp. 117–122.*
Moch, C, et al, 2001, Divergence between the high rate of p53 mutations in skin carcinomas and the low prevalence of anti–p53 antibodies, British Journal of Cancer, vol. 85, No. 12, pp. 1883–1886.*
Broll, R, et al, 2001, p53 autoantibodies in sera of patients with a colorectal cancer and their association to p53 protein concentration and p53 immunohistochemistry in tumor tissue, Int. J. Colorectal Dis., vol. 16, No. 1, pp. 22–27.*
S. Zrihan–Licht et al., "Association of Csk–homologous kinase (CHK) (formerly MATK) with HER–2/ErB–2 in breast cancer cells". Journal of Biological Chemistry, vol. 272, No. 3, (Jan. 17, 1997) pp. 1856–1863.
M. Chedin et al., "Characterization of two different cytoplasmic protein tyrosine kinases from human breast cancer". Chemical Abstracts, vol. 127, No. 18, (Nov. 3, 1997), Abstract No. 244619.

* cited by examiner

Primary Examiner—Anthony C. Caputa
Assistant Examiner—Stephen L. Rawlings
(74) Attorney, Agent, or Firm—Piper Rudnick LLP

(57) ABSTRACT

The invention concerns a method for early diagnosis of cancer in a patient which consists in identifying by any appropriate method the presence of autoantibodies directed against the Csk protein in a biological sample taken from said patient. The invention also concerns a kit for implementing said diagnostic method.

12 Claims, 1 Drawing Sheet

PATIENT I.D. NUMBER
| 1 | 2 | 3 |
|---|---|---|
| Bladder | Colon | Colon |
C   T     C   T     C   T
 ←Csk
From the serum
of a patient
Anti-Csk autoantibody
present ?        YES         YES          NO
C = Healthy Tissue
T = Tumor Tissue

METHOD AND KIT FOR EARLY DIAGNOSIS OF CANCER

RELATED APPLICATION

This is a continuation of International Application No. PCT/FR99/01444, with an international filing date of Jun. 16, 1999, which is based on French Patent Application No. 98/07655, filed Jun. 17, 1998.

FIELD OF THE INVENTION

This invention relates to the field of cancer screening and monitoring.

BACKGROUND

A major problem in the treatment of cancer remains its early detection. Early detection enables therapeutic treatment from the onset of the disease resulting in successful treatment in many cases.

Numerous studies have demonstrated that tumour cells can express substances liable to be detected in blood and, as a result, liable to be used as tumour markers. It is possible to distinguish between two main types of such substances:

Substances related to tumour presence but which are not involved in tumour formation. Said substances include various proteins (mucins, CA 15-3 and CA 125 markers), protein fragments (cytokeratin fragments, CYFRA 21 marker), enzymes (neurospecific enolase, NSE marker), or oncofoetal antigens such as carcinoembryonic antigens and ACE markers. Such substances, present in normal cells, are altered by the tumoral activity and/or have access to the extracellular compartment due to tumoral necrosis. The detection of such substances is already widely used in clinical practice. However, they only appear when the tumour is established and, as a result, cannot be detected at an early stage.

Substances directly related to tumour formation. Such substances particularly include P53 protein which is produced by a tumour-suppressing gene, and is altered and/or overexpressed in tumours. This alteration and/or overexpression results in a modification of DNA repair control and a higher susceptibility of cells to cell transformation (see T. Soussi et al., 1994; Int. J. Cancer: 57, 1–9). Therefore, P53 protein alterations are the source of tumour formation, in which they represent an early stage. In addition, the presence of autoantibodies directed against P53 protein has been detected in the serum of patients suffering from cancer and the detection of said autoantibodies is under clinical study (C. P. Wild et al., 1995, Int. J. Cancer (Pred. Oncol.): 64, 176–181).

Therefore, substances directly related to tumour formation, such as P53 protein or autoantibodies directed against such protein represent effective cancer markers. However, in view of the increasingly rapid set-up of treatments, it is still necessary to identify new earlier markers. In addition, the markers already described, such as P53 protein, are characteristics of certain types of tumours and are, therefore, not sufficiently polyvalent to diagnose all types of cancer.

SUMMARY OF THE INVENTION

The invention relates to a diagnostic process for detecting cancer in a patient including identifying the presence of anti-Csk autoantibodies in a biological sample obtained from the patient. The invention also relates to a diagnostic kit for cancer diagnosis in a biological sample of a subject including Csk protein or a modified form, fragment(s) or conjugates of the substances, reagents to create a medium favorable to an immunological reaction between the Csk proteins or a modified form, fragment(s) or conjugates of the substances and the anti-Csk autoantibodies possibly present in the biological specimen, and one or more reagents which react with Csk proteins or a modified form, fragment(s) or conjugates of said substances and/or anti-Csk autoantibodies and/or immunological complexes, to detect immunological complexes possibly formed.

BRIEF DESCRIPTION OF THE DRAWING

The drawing shows endogenous Csk protein in healthy tissue C and tumour tissue T of three patients.

DETAILED DESCRIPTION

This invention specifically relates to a new cancer marker at an earlier stage than the P53 protein and enables detection of cancer for which the P53 protein is not a marker.

Our research makes it possible to demonstrate the presence, in the serum of subjects suffering from cancer, of autoantibodies directed against a tyrosine kinase type enzymatic activity cytoplasmic protein referred to a Csk for "C-terminal Src Kinase". Csk protein has been known for a long time and its gene has been cloned and sequenced (S. Nada et al., 1991, Nature 351, 69–72; Braüniger et al., Proc. Natl. Acad. Sci. USA, 1991, 88:10411–10415). Csk protein is involved in the negative regulation of the activity of Src family tyrosine kinase enzymes (Okada et al., J. Biol. Chem., 1991, 266:24249–24252; Nada et al., Cell, 1993, 73:1125–1135). Src family enzymes are produced by cellular proto-oncogenes and are involved in the regulation of numerous biological functions, particularly cell growth (Roche et al., Science, 1995, 269:1567–1569). Overexpression or deregulation of such enzymes induces the formation of tumours in animals. In humans, it has been demonstrated that Src family enzymes are activated and/or overexpressed in different types of cancer: colon cancer (Cartwright et al., Proc. Natl. Acad. Sci. USA, 1990, 87:558–562), melanoma (Loganzo et al., Oncogene, 1993, 8:2637–2644), breast cancer (Lutrell et al., Proc. Natl. Acad. Sci. USA, 1994, 91:83–87; Chedin et al., Carcinogenesis, 1997, 18:1463–1472), colon and ovarian cancer (Budde et al., Cancer Biochemistry and Biophysics, 1994, 14:171–175), bladder cancer (Bénistant et al., Biochim. Biophys. Res. Comm., 2000, 273,425–430). In addition, while Csk represents a negative Src family enzyme regulator, paradoxically, Csk overexpression has also been demonstrated in tumours (Chedin et al., Carcinogenesis, 1997, 18:1463–1472).

By analogy with the research conducted on P53 protein, the inventors now tested in the serum of the subjects under study for the possible presence of autoantibodies directed against Src and Csk proteins. This study was audacious since numerous other gene products are known to accumulate in tumours (H-ras, ki-ras, myc, erb2, etc.) without inducing autoantibody generation and, apart from P53 protein, the presence of autoantibodies has never been demonstrated for proteins involved in cell regulation in cancerous subjects. Therefore, detection of such antibodies represents a genuine discovery.

In addition, the fact that, firstly, anti-Csk autoantibodies exist in some patients, and, secondly, that the Src enzyme is activated in the same patients, suggests very strongly that the Csk gene could be mutated in tumours. In this way, the mutated Csk protein appears to represent an element unknown to the body inducing the mobilisation of the immune system as seems to be the case for P53 protein. In addition, mutated Csk protein appears to no longer play its role as a negative Src family enzyme regulator and then becomes oncogenic. In addition, it is not impossible that Csk could have other functions in the cell, which could be altered by a mutation of Csk, or mutated Csk acts on other substrates than Src family enzymes thus disturbing various biological functions resulting in cell transformation.

Therefore, this invention relates to an early cancer diagnostic process in a patient consisting of identifying by any appropriate process the presence of autoantibodies directed against a Csk protein in a biological specimen obtained from such a patient.

The term Csk protein refers to not only the Csk protein (S. Nada et al., 1991, Nature 351, 69–72; Brauniger et al., Proc. Natl. Acad. Sci. USA, 1991, 88:10411–10415), but also Csk family enzymes such as that referred to, depending on the authors, as Ctk, Ntk, Chk, Matk (Klages et al., Proc. Natl. Acad. Sci. USA, 1994, 91:2597–2601; Chow et al., Proc. Natl. Acad. Sci. USA, 194, 4975–4979; Davidson et al., J. Biol. Chem., 1997, 272:1856–1863), hereafter referred to for convenience as "Ctk." Ctk protein is produced by a gene other than that of Csk, but the detection of anti-Ctk autoantibodies also comes within the scope of this invention.

A particularly appropriate process to identify the presence of anti-Csk autoantibodies according to the invention is based on an immunological reaction between such autoantibodies and Csk proteins, or a modified form, fragment(s) or conjugates of such substances, such as the ELISA technique, for example. This technique consists of adsorbing, at the base of ELISA plate wells, Csk protein and a reference protein (BSA, for example), then, after washing, placing the proteins in contact with serum specimens from patients under test liable to contain anti-Csk autoantibodies to produce an immunological reaction between the Csk proteins and Csk autoantibodies, and detecting the immunological complexes possibly formed by appropriate means to determine the presence or absence of anti-Csk autoantibodies in the specimens under test.

Conventionally, an appropriate means to detect the immunological complexes possibly formed consists of using a human anti-IgG antibody bound with peroxidase, which is capable of fixing on the complexes possibly formed, and then, after adding peroxidase substrate, measuring the coloured reaction by measuring the absorbance at 405 nm, the intensity of which is proportional to the quantity of antibodies present.

The terms "modified form" or "fragment(s)" of Csk protein refers to any proteins and any polypeptides or peptides for which the amino acid sequence is obtained from that of Csk protein, once they retain the ability to form specific immunological complexes with anti-Csk autoantibodies. The term "Csk protein conjugate" refers to a modified form of fragment(s) of said protein, bonding products with a molecule or a carrier substance.

The invention also relates to the use of Csk protein or a modified form, fragment(s), conjugates or derivatives thereof of said substances to detect anti-Csk autoantibodies in a biological specimen of a subject.

The Csk protein, a modified form or fragment(s) of said proteins may be obtained by purification from tissues possibly followed by splitting or treatment aiming to modify the sequence, or be produced by genetic engineering using an appropriate expression system such as a baculovirus/insect cell system (M. Koegl et al., Biochem. J., 1994, 302, 737–744).

The process according to the invention offers the advantage of possible use on the serum of subjects enabling significantly easier implementation with reference to biopsy analyses. In addition, as reported in the experimental section below, it enables a very early diagnosis of tumour presence, earlier than a diagnosis with conventional markers such as ACE, CA153 or even P53 protein.

The process according to the invention enables the early diagnosis of a very large number of types of cancer and more particularly types of cancer wherein Src protein is activated: colon cancer (Cartwright et al., Proc. Natl. Acad. Sci. USA, 1990, 87:558–562), melanoma (Loganzo et al., Oncogene, 1993, 8:2637–2644), breast cancer (Lutrell et al., Proc. Natl. Acad. Sci. USA, 1994, 91:83–87; Chedin et al., Carcinogenesis, 1997, 18:1463–1472), colon and ovarian cancer (Budde et al., Cancer Biochemistry and Biophysics, 1994, 14:171–175), bladder cancer (Benistant et al., under preparation). This essentially relates to epithelial cancer, i.e., all cases of carcinoma which is the most frequent type of cancer, some types of melanoma and some types of breast cancer. In addition, the process according to the invention which enables early screening for cancer should make it possible to detect patients carrying colic polyps undergoing tumoral transformation. Conversely, it is possible that the process according to the invention will not enable the detection of cancer wherein Src protein is not activated, such as small cell lung cancer (Budde et al., Cancer Biochemistry and Biophysics, 1994, 14:171–175). This gives the process according to the invention a certain specificity.

More specifically, the invention relates to an early breast cancer diagnostic process in a patient consisting of identifying by a appropriate method, as described above, the presence of autoantibodies directed against the Ctk protein in a biological specimen taken from the patient. Ctk protein, which is of Csk type, shows a very specific tissue or intracellular distribution, the expression of which is induced specifically in breast cancers (Zrihan-Licht et al., J. Biol. Chem., 1997, 272:1856–1863).

The invention also relates to a diagnostic kit for the use of an early cancer diagnostic process comprising:

Csk protein or a modified form, fragment(s) or conjugates of said substances;

reagents to create a medium favourable to the immunological reaction between the Csk proteins or a modified form, fragment(s) or conjugates of the substances and the anti-Csk autoantibodies possibly present in a biological specimen;

one or more reagents labelled, if required, capable of reacting with Csk proteins or a modified form, fragment(s) or conjugates of said substances and/or anti-Csk autoantibodies and/or immunological complexes, to detect said immunological complexes possibly formed;

if applicable, a reference protein or a reference biological medium.

The reference protein is, for example, BSA, and the reference biological medium consists of, for example, sera of patients showing three levels of responses: weak, moderate, strong.

Other advantages and characteristics of the invention can be seen in the description of the experimental research resulting in the invention.

I—Detection of the existence of anti-Csk autoantibodies and their interest as early cancer markers.

1) Detection and specificity of anti-Csk autoantibodies.

Csk antigen proteins and two members of the Src family (Src and FYN), and the BSA control protein, were placed in wells of ELISA plates at the same concentration of 10 μg/ml. Then, the sera diluted to 1/20 of two healthy patients (controls), four patients suffering from colon cancer at different anatomopathological stages and one patient suffering bladder cancer at an early stage were then added. The analyses were conducted in duplicate. The results representing the absorbance values at 405 nm measured in a typical experiment are shown in Table I below.

TABLE I

| Subjects tested | Src antigen | FYN antigen | BSA antigen | Csk antigen |
|---|---|---|---|---|
| Control | 0.275 | 0.274 | 0.242 | 0.336 |
| Control | 0.289 | 0.279 | 0.263 | 0.281 |
| Colon cancer No. 1 stage C | 0.349 | 0.259 | 0.262 | 0.321 |
| Colon cancer No. 2 stage B | 0.276 | 0.267 | 0.250 | 0.789 |
| Colon cancer No. 3 stage D | 0.345 | 0.248 | 0.273 | 0.290 |
| Colon cancer No. 4 stage B | 0.310 | 0.280 | 0.271 | 0.375 |
| Bladder cancer No. 5 stage PTa | 0.322 | 0.283 | 0.215 | 1.360 |

It is noted that the controls, and patients 1, 3 and 4 produce a weak response irrespective of the antigen. However, patients 2 and 5 produce a strong response to Csk antigen. This response is specific since that obtained with the other antigens is weak. Overall, the values measured for Src, FYN and BSA antigens are similar. In this way, for simplification purposes, the series of tests was conducted using only BSA antigen (commercial) as the negative control. The two patients considered to be positive in this first test suffered from a relatively early stage of cancer: stage B colon cancer (Dukes classification) and stage PTa bladder cancer (international classification). Finally, those two patients belong to both sexes: patient 2 was female and patient 5 was male.

It is important to note that all three Src, FYN and Csk antigens were produced and purified according to the same protocol. Since the antigenic response was only observed with reference to Csk, it is clear that the results obtained cannot be due to the difference in the preparation method or origin of the antigenic proteins. In addition, the specificity of the circulating antibody/Csk antigen bond was tested on sera of positive patients by conducting a displacement study in vitro. In this experiment, the serum of positive patients was placed in contact with Csk and BSA antigens, and Csk or BSA in solution (10 or 100 μg/ml) were then added. In the presence of Csk (10 μg/ml), a decrease in absorbance was observed. With 100 μg/ml of Csk protein, the absorbance returns to the base value. Under the same conditions, BSA protein has no effect. This confirms that the anti-Csk autoantibodies were specific for Csk antigen.

2) Anti-Csk autoantibodies can be used to detect cancer specifically.

The presence of anti-Csk anti-antibodies was tested for in 92 patients suffering from various forms of cancer, 30 cases of colorectal cancer, 17 cases of bladder cancer, 7 cases of small-cell lung cancer, 21 cases of breast cancer, 10 cases of ovarian cancer and in 40 blood donor controls considered to be healthy and in 21 patients suffering from other diseases (11 patients suffering from autoimmune thyroid diseases and 10 patients suffering from various non-cancerous gastrointestinal disorders). The ELISA tests were conducted with respect to Csk protein, using BSA in parallel as the negative control. All the measurements were made in duplicate or quadruplicate. The serum of patient 5 who had the strongest response in Table 1 was included systematically in each of the assay plates as a positive control, the absorbance of said serum with respect to Csk always exceeding the value of 1.2.

It is important to note that the absorbance of serum in the ELISA test remained constant for a long period of time which demonstrates the stability of the anti-Csk autoantibodies. The mean of the values obtained for each serum and for each of the experimental conditions was calculated. The absorbance values with respect to BSA were less than 0.4 in 90% of cases. Subjects with an absorbance with respect to Csk of greater than 0.4 and with a Csk/BSA absorbance ratio greater than 1.3 were considered to be positive, as described for anti-P53 autoantibody detection (C.P. Wild et al., 1995, Int. J. Cancer (Pred. Oncol.): 64, 176–181). The results obtained are shown in Table 2 below.

TABLE 2

| Population | Number of positive patients/ Number tested | % |
|---|---|---|
| Colorectal cancer | 6/30 | 20 |
| Bladder cancer | 3/17 | 18 |
| Pulmonary adenocarcinoma | 1/7 | 14 |
| Small-cell lung cancer | 0/7 | 0 |
| Breast cancer | 1/21 | 5 |
| Ovarian cancer | 1/10 | 10 |
| Healthy blood donors | 0/40 | 0 |
| Other diseases | 0/21 | 0 |

The results presented in Table 2 show that the test is specific for cancer. Indeed, none of the controls and none of the patients suffering from non-cancerous diseases such as those suffering from autoimmune thyroid diseases with a high antithyroid autoantibody concentration produce a positive response. However, patients were detected in all the types of cancer tested, except for those suffering from small-cell lung cancer. This result could be related to the low number of samples or the fact that Csk protein is not involved in this type of tumour.

3) The anti-Csk autoantibody level falls after tumour resection.

Some of the patients suffering from colon cancer who were tested in this study were in parallel in an another P53 analysis protocol and the sera had been sampled at the pre- and postoperative stages. Of the six patients positive for anti-Csk autoantibodies reported in Table 2, three were monitored in this way. The results obtained are given in Table 3 below which gives the OD values obtained with respect to Csk antigen. These results show a decrease in the anti-Csk autoantibody level in the serum of the patients after tumour resection.

TABLE 3

| Patients | Preoperative | Postoperative |
|---|---|---|
| 1 | 0.583 | 0.496 |
| 2 | 0.526 | 0.318 |
| 3 | 1.256 | 0.444 |

These results confirm that the anti-Csk autoantibodies are specific for cancer, since the patients in question were operated on for this disease. These results demonstrate the interest also offered by the anti-Csk autoantibody assay in patient monitoring.

4) Anti-Csk autoantibodies are present in patients suffering from early stages of cancer.

The distribution of positive patients versus the number of patients tested as a function of the tumour progression stage and for cases of colorectal and bladder cancer are shown in Table 4 below.

TABLE 4

| Stage | Early | Late |
|---|---|---|
| colorectal | 4/15 | 2/15 |
| bladder | 3/17 | 0/17 |

The highest frequency of detection is observed for the early tumoral stages: stages A and B colon cancer according to Dukes classification and stages PTa and Pt1 bladder cancer according to the international classification.

5) Type of immunoglobulins involved.

To identify the type of immunoglobulins involved, the reactivity of the following immunoglobulin classes: IgGFc, IgG1, IgG2, IgG3, IgG4, IgGA and IgGM bound with peroxidase were tested in 3 positive patients. Table 5 below shows the OD values obtained with respect to Csk antigen.

TABLE 5

| IgG type | IgGFc | IgG1 | IgG2 | IgG3 | IgG4 | IgGM | IgGA |
|---|---|---|---|---|---|---|---|
| Patient 1 | 0.453 | 0.288 | 0.221 | 0.172 | 0.144 | 0.551 | 0.205 |
| Patient 2 | 0.459 | 0.189 | 0.155 | 0.137 | 0.134 | 0.502 | 0.170 |
| Patient 3 | 1.962 | 1.313 | 0.245 | 0.123 | 0.082 | 0.585 | 0.410 |

The majority class in 2 out of 3 patients in the, IgGM class, which supports the fact that anti-Csk autoantibodies are produced by an early immune phenomenon. In patient 3, who produces a very strong response, amplification of the immune response and generation of IgGl type antibodies are observed.

6) Anti-Csk autoantibodies are observed in patients actually showing a rise in the level of their Csk protein in tumour tissue in comparison to healthy tissue.

The study was conducted on specimens of healthy tissue, sampled at a distance from the tumour, and on specimens sampled directly on the tumour of the patients. The endogenous Csk protein content in said tissues was analysed with the Western Blot technique.

FIG. 1 appended shows the endogenous Csk protein in the healthy tissue C and tumour tissue T of 3 patients: in 1 bladder, in 2 and 3 colon. It is observed that the endogenous Csk protein content of patient 5 in Table 1 and one of the positive patients suffering from colon cancer in Table 2 increases considerably in the tumour tissue T in comparison to the healthy tissue C. On the other hand, the Csk content of a patient negative for anti-Csk anti-autoantibodies is unchanged.

II—Benefits of anti-Csk autoantibody assay.

The 30 patients suffered from colon cancer studied within the scope of the present invention were also enrolled in a study protocol on P53 autoantibody detection.

The conventional tumour markers, ACE and CA 19.9, of said patients were also determined. The data from the different tests is shown in Table 6 below.

TABLE 6

| Patients | Early stage | ACE | CA 19.9 | P 53 | Csk |
|---|---|---|---|---|---|
| 1 | A | − | − | + | + |
| 2 | A | − | − | − | − |
| 3 | B | − | − | − | − |
| 4 | B | nd | nd | − | − |
| 5 | B | − | − | − | − |
| 6 | B | − | − | − | + |
| 7 | B | − | − | − | − |
| 8 | B | − | − | − | − |
| 9 | B | − | + | − | + |
| 10 | B | + | + | − | − |
| 11 | B | − | − | − | − |
| 12 | B | + | + | − | − |
| 13 | B | − | − | − | − |
| 14 | B | nd | nd | − | − |
| 15 | C | − | − | + | + |
| | Late | | | | |
| 16 | C | − | − | − | − |
| 17 | C | − | − | + | − |
| 18 | C | − | + | − | − |
| 19 | C | − | − | − | + |
| 20 | C | + | − | − | − |
| 21 | C | nd | nd | − | − |
| 22 | C | nd | nd | − | − |
| 23 | C | + | + | − | − |
| 24 | C | − | − | − | + |
| 25 | C | + | + | − | − |
| 26 | D | − | + | + | − |
| 27 | D | + | + | − | − |
| 28 | D | − | − | + | − |
| 29 | D | + | + | + | − |
| 30 | D | − | − | + | − |

(nd: not determined)

Table 6 shows that none of the markers enable absolute screening for colorectal cancer. However, this table shows that the Csk test makes it possible, firstly, to detect patients suffering from cancer who are not detected with any of the other tests (patients 6, 19 and 24) and, secondly, to diagnose more cases of cancer at an early stage.

It is important to note that the patients tested suffering from other types of cancer, such as lung, ovarian or breast cancer, illustrated in Table 2, were selected since they all carry the respective markers of their type of cancer (CYFRA 21, CA125, CA15.3). Therefore, these patients are certain to develop cancer. However, since the Csk autoantibody assay is a screening test for the early stages of the disease, the low number of patients detected may be explained by the fact that the stage of the cancer of these patients is too advanced.

What is claimed is:

1. A diagnostic process for detecting epithelial cancer in a patient comprising:
   identifying the presence of autoantibodies against Csk in a biological sample obtained from said patient and, such that if said anti-Csk autoantibodies are present, the patient is determined to have epithelial cancer,
   wherein said epithelial cancer is selected from the group consisting of colorectal cancer, bladder cancer, pulmonary adenocarcinoma, breast cancer, and ovarian cancer.

2. The method of claim 1, wherein said epithelial cancer is colorectal cancer.

3. The method of claim 1, wherein said epithelial cancer is bladder cancer.

4. The method of claim 1, wherein said epithelial cancer is ovarian cancer.

5. The method of claim 1, wherein said epithelial cancer is breast cancer.

6. The process according to claim 1, wherein the presence of said autoantibodies is identified by observing formation of a specific immune complex comprising the autoantibodies and Csk in an enzyme-linked immunosorbent assay (ELISA).

7. The process of claim 6, wherein Csk is detectably labeled.

8. A method for detecting anti-Csk autoantibodies in a subject comprising:
   adding together Csk and a biological sample obtained from a subject, and
   observing the formation of a specific immune complex comprising the autoantibodies and Csk in an ELISA, such that if said formation is observed, said autoantibodies are present in the said sample.

9. A method for detecting epithelial cancer in a patient which comprises:
   a) contacting a biological sample obtained from a patient and Csk; and
   b) detecting the presence of a specific immune complex comprising Csk and anti-Csk autoantibodies, such that if said immune complex is detected, said anti-Csk autoantibodies are present in said sample and the patient is determined to have epithelial cancer,
   wherein said epithelial cancer is selected from the group consisting of colorectal cancer, bladder cancer, pulmonary adenocarcinoma, breast cancer, and ovarian cancer.

10. The method of claim 9, wherein the method is an enzyme-linked immunosorbent assay (ELISA).

11. The method of claim 9, wherein said immune complex comprising anti-Csk autoantibodies is detected radioisotopically, euzymatically, fluorogenically, chemiluminescently or electrochemically.

12. The method of claims 8 or 9, wherein Csk is detectably labeled.

* * * * *